United States Patent
Grammenos et al.

(10) Patent No.: US 6,344,589 B1
(45) Date of Patent: Feb. 5, 2002

(54) METHOD AND INTERMEDIATE PRODUCTS FOR PRODUCING BIS(OXIME) MONOETHERS

(75) Inventors: Wassilios Grammenos, Ludwigshafen; Hubert Sauter, Mannheim; Andreas Gypser, Mannheim; Herbert Bayer, Mannheim; Norbert Götz, Worms; Roland Götz, Neulussheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,970
(22) PCT Filed: Nov. 12, 1999
(86) PCT No.: PCT/EP99/08742
  § 371 Date: May 3, 2001
  § 102(e) Date: May 3, 2001
(87) PCT Pub. No.: WO00/31024
  PCT Pub. Date: Jun. 2, 2000

(30) Foreign Application Priority Data

Nov. 20, 1998 (DE) .......................... 198 53 705

(51) Int. Cl.$^7$ ............................................ C07C 249/00
(52) U.S. Cl. ........................................ 564/256; 564/259
(58) Field of Search .................................. 564/256, 259

(56) References Cited

U.S. PATENT DOCUMENTS 4,260,762 A 4/1981 Berger et al.

FOREIGN PATENT DOCUMENTS

| DE | 1 137 434 | 10/1962 |
| EP | 10 661 | 5/1980 |
| GB | 821 400 | 10/1959 |
| GB | 999 778 | 7/1965 |

OTHER PUBLICATIONS

XP–002130256, The Behaviour of Unsaturated 1, 2–Hydroxyiminoketones With Trifluoroacetic Acid, Bishop et al., 6805–6808, 1988.

*Primary Examiner*—Samuel Barts
(74) *Attorney, Agent, or Firm*—Keil & Weinkauf

(57) ABSTRACT

A process for preparing bis(oxime) monoethers of the formula I,

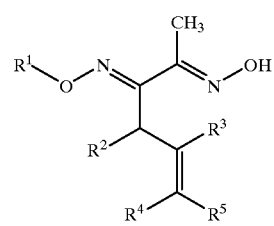

where:
  $R^1$ is unsubstituted $C_1$–$C_4$-alkyl or $C_2$–$C_4$-alkenyl-, $C_2$–$C_4$-alkynyl- or phenyl-substituted methyl;
  $R^2, R^4$ independently of one another are hydrogen or methyl;
  $R^3, R^5$ independently of one another are hydrogen or $C_1$–$C_4$-alkyl, trifluoromethyl or phenyl,
and intermediates which are obtainable by this process are described.

4 Claims, No Drawings

METHOD AND INTERMEDIATE PRODUCTS FOR PRODUCING BIS(OXIME) MONOETHERS

This application is a 371 of PCT/EP99/08742 filed Nov. 12, 1999.

The present invention relates to a process for preparing bix(oxime) monoethers of the formula I,

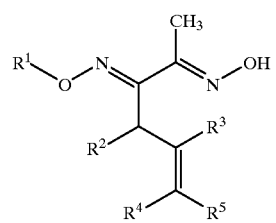

where:
- $R^1$ is unsubstituted $C_1$–$C_4$-alkyl or $C_2$–$C_4$-alkenyl-, $C_2$–$C_4$-alkynyl- or phenyl-substituted methyl;
- $R^2, R^4$ independently of one another are hydrogen or methyl;
- $R^3, R^5$ independently of one another are hydrogen or $C_1$–$C_4$-alkyl, trifluoromethyl or phenyl.

Moreover, the invention relates to monooximes of the formula III and

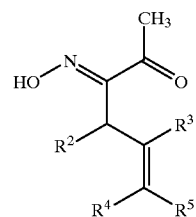

mono(oxime ethers) of the formula IV

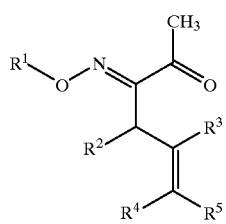

which are obtainable by this process. Bis(oxime) monoethers of the formula I and mono(oxime ethers) of the formula IV are interesting intermediates for preparing the fungicidal crop protection agents known from WO-A 95/21153, WO-A 95/21154 and WO-A 97/03057.

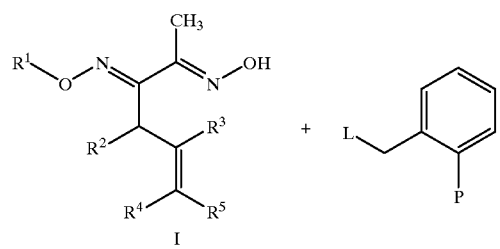

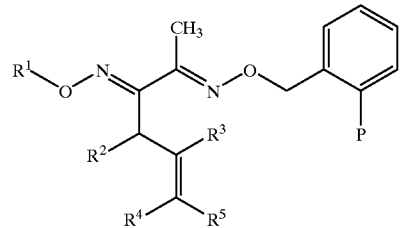

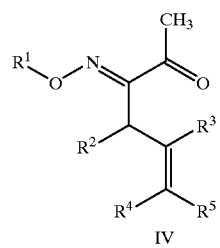 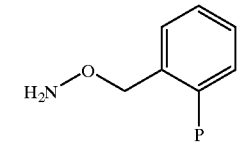 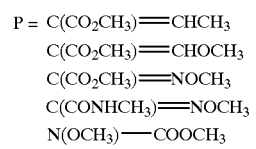

P = C(CO$_2$CH$_3$)=CHCH$_3$
C(CO$_2$CH$_3$)=CHOCH$_3$
C(CO$_2$CH$_3$)=NOCH$_3$
C(CONHCH$_3$)=NOCH$_3$
N(OCH$_3$)—COOCH$_3$

In the prior art, the synthesis specifically of the alkenylalkyl-substituted dione derivatives I and IV has not been described (cf. WO-A 95/21153, WO-A 95/21154, WO-A 96/16030 and WO-A 97/03057). The general schemes in these publications show only synthesis routes starting from (α-diketones a) or the corresponding α-bis-oximes b) (see scheme 1).

Scheme 1

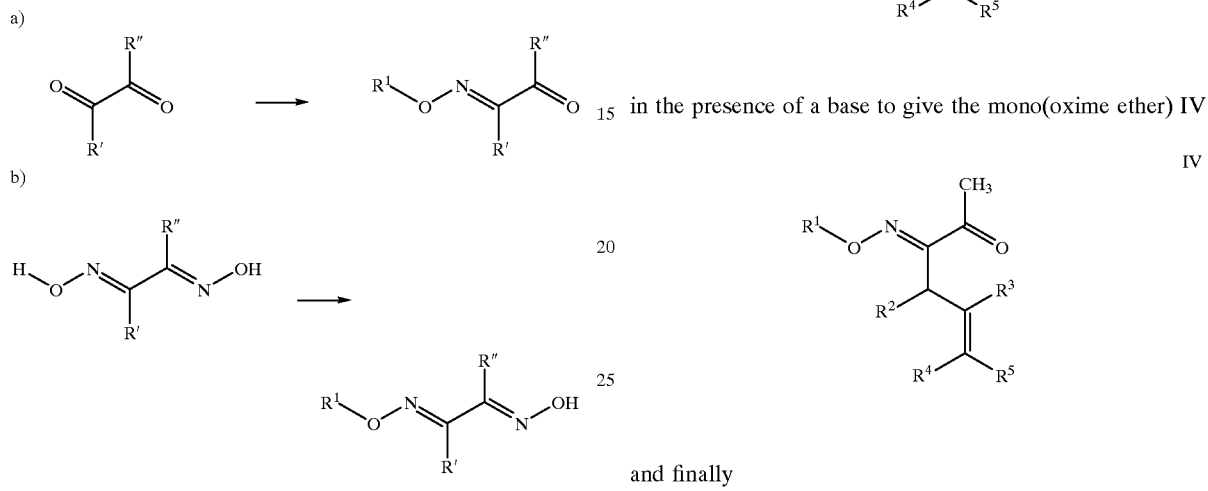

Owing to the bifunctionality, substance mixtures are to be expected as products a) in the oximation of the α-diketones and b) in the alkylation of the α-bisoximes. In addition to the desired monocondensation/substitution product, the unreacted and the doubly reacted product are generally also found in reactions of this type.

However, in the present case there is another more serious problem. The alkenylalkyl radical (which corresponds to $R^1$ in scheme 1) is much more sterically demanding than the methyl radical (R''). Any monocondensation/substitution product formed would presumably have the wrong regio- and stereochemistry (cf. Liebigs Ann. Chem. (1974) 1908–1914). The sequence shown in scheme 1 is therefore unsuitable for synthesizing bis(oxime) monoethers of the formula I.

It is an object of the present invention to provide a process which allows the targeted synthesis of compounds of the formulae I and IV.

We have found that this object is achieved by the process mentioned at the outset, which comprises a) treating an acetoacetic ester of the formula II

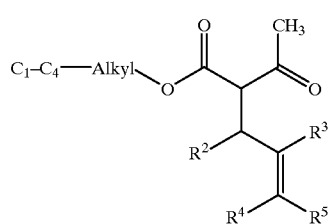

II with a nitrite initially under alkaline conditions and subsequently under acid conditions and b) alkylating the resulting monooxime III

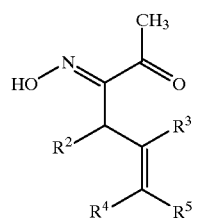

III in the presence of a base to give the mono(oxime ether) IV

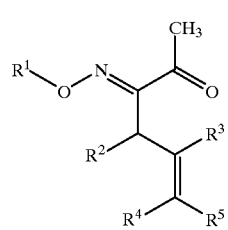

IV and finally c) reacting the mono(oxime ether) IV with hydroxylamine or its acid addition salt to give the bis(oxime) monoether I.

The process according to the invention is illustrated using the synthesis of hex-5-ene-2,3-dione 3-(O-methyloxime) 2-oxime as an example (see scheme 2).

Scheme 2

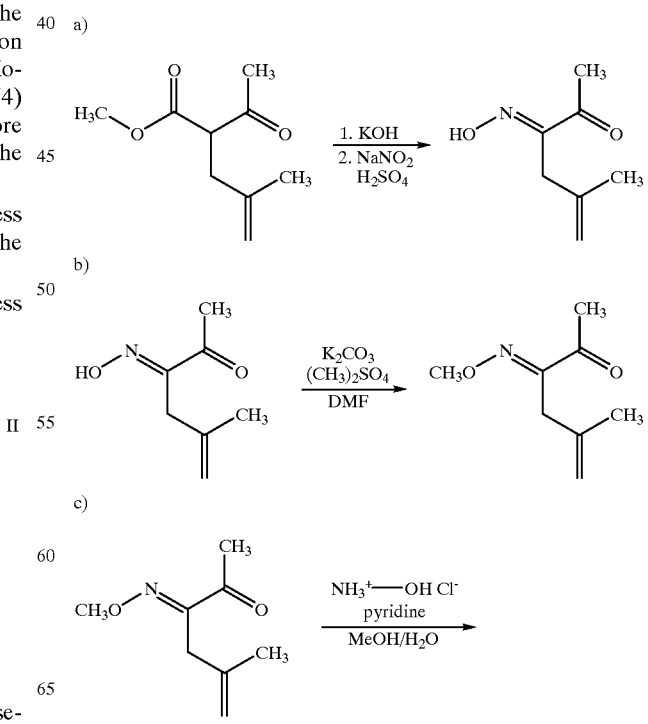

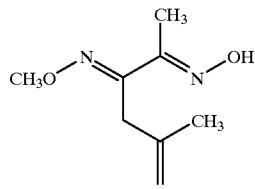

The individual steps of the process according to the invention are illustrated in more detail below.

Step a):

Step a) is carried out using the method of the procedure described in U.S. Pat. No. 4,707,484.

Alcohols, such as, for example, methanol, and in particular water may serve as solvent. In certain cases it may be advantageous to add solubilizers, such as, for example, surfactants or ethylene glycol.

Suitable bases are, in particular, sodium hydroxide and potassium hydroxide, which are usually employed in equimolar amounts or in an up to ten-fold molar excess, based on the acetoacetic ester II.

Nitrite is to be understood as, for example, an alkali metal nitrite, in particular sodium nitrite, which is usually employed in equimolar amounts or in an excess of up to 30 mol %, based on the acetoacetic ester II.

In general, the reaction temperature should not exceed 40° C. since otherwise undesirable side reactions occur. In water, the reaction is therefore preferably carried out at from −20 to 40° C., in particular at from 0 to 15° C.

After a period of from 10 to 48 hours, the reaction mixture usually becomes clear. A pH of from 0 to 5 and preferably of from 1 to 3 is then established using an acid, such as, for example, hydrochloric acid or sulfuric acid.

Work-up is carried out by customary methods, for example by extraction. For purification, the oxime can, for example, be converted into the corresponding salt using bases and precipitated again using an acid.

The acetoacetic ester II employed for the reaction can be prepared as described in Tetrahedron (1985) 4633 (see scheme 3).

Scheme 3

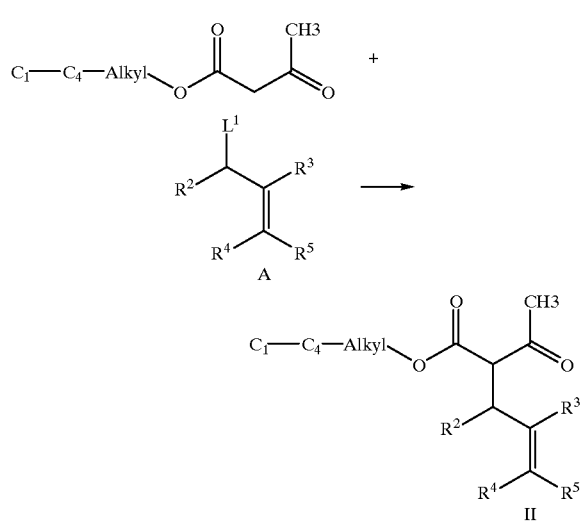

The alkenylalkyl compounds of the formula A in which $R^2$ to $R^5$ are as defined in claim 1 and $L^1$ is halogen, acyloxy, alkylsulfonyloxy or arylsulfonyloxy are known or can be synthesized by processes known from the literature (Z. Org. Khim. (1997) 486; Bull. Chem. Soc. Jpn. (1980) 2586; J. Am. Chem. Soc. (1984) 2211; J. Am. Chem. Soc. (1960) 1886; DE-A 19 556 66; DE-A 33 173 56; EP-A 271212; Tetrahedron Let. (1986) 6027; Tetrahedron Let. (1994) 1371 and 2679; J. Fluorine Chem. (1997) 67; Helv. Chim. Acta (1951) 1514; Organomnet. Chem. (1985) 395).

Step b):

The alkylation is usually carried out in the presence of an inert organic solvent. Suitable solvents are, inter alia, aliphatic or aromatic hydrocarbons, such as, for example, toluene, xylene, heptane or cyclohexane, aliphatic or cyclic ethers, such as, for example, 1,2-dimethoxyethane, tetrahydrofuran or dioxane. Preference is given to using polar aprotic solvents: ketones, such as, for example, acetone, nitriles, such as, for example, acetonitrile, amides, such as, for example, dimethylformamide, dimethylacetamide or N-methylpyrrolidone, or ureas, such as tetramethyl urea.

The alkylating agent used is usually a halide, preferably a chloride or bromide, a sulfate, preferably dimethyl sulfate, a sulfonate, preferably a methanesulfonate (mesylate) or a toluene sulfonate (tosylate).

The amount of base or alkylating agent is preferably from one to two times the equimolar amount, based on the compound III.

In general, the reaction is carried out in the presence of an inorganic base, such as sodium hydroxide or potassium hydroxide, sodium carbonate or potassium carbonate, sodium bicarbonate or potassium bicarbonate, or of an alkali metal alkoxide, such as sodium methoxide or potassium tert-butoxide.

The reaction temperature is generally at from 0° C. to 50° C., preferably from 0° C. to 40° C. and in particular at room temperature.

Work-up can be carried out, for example, by extraction.

To remove residual amounts of alkylating agent, it may be advantageous to wash the reaction batch with, for example, ammoniacal solution.

Step c):

Hydroxylamine is employed either in the form of an acid addition salt or as free base, it being possible to liberate the latter from the salt by addition of a strong base.

Preference is given to using the acid addition salts of the hydroxylamine. All customary acids are suitable for preparing the acid addition salts. Just a few of them are listed below, by way of example: carboxylic acids, such as acetic acid or propionic acid, dicarboxylic acids, such as oxalic acid or succinic acid, mineral acids, such as phosphoric acid or carbonic acid and in particular hydrochloric acid or sulfuric acid.

If the acid addition salts of the hydroxylamine are employed, it is generally advantageous to add a base to bind the acid liberated in the reaction. In many cases, a pH of from 3 to 7 and in particular of from 4 to 6 has been found to be advantageous for the oximation. Outside these pH ranges, side reactions such as ring closure reactions may occur.

In general, 1 to 2.5 molar equivalents of a base are added.

Suitable bases are, in particular, pyridines, trialkylamines, sodium hydroxide, sodium acetate and sodium methoxide. If sodium acetate is employed, it is customary to add glacial acetic acid.

Conversely, it is of course also possible to employ the hydroxylamine as free base and to use one of the above-mentioned acids to establish the abovementioned pH range.

Solvents which can be employed are, for example, those described in the previous step. Other suitable solvents are carboxylic acids, such as acetic acid, or else water/pyridine mixtures. Alcohols, such as methanol, ethanol, n-propanol or isopropanol, and mixtures of these with water and/or pyridine are particularly suitable.

The reaction temperature is generally from −20 to 100° C., preferably from 0 to 40° C. and in particular from 20 to 25° C.

Work-up of the reaction mixture is preferably carried out by extraction, as described in the previous step. To remove the base completely, it may be advantageous to wash the crude product first, with a dilute aqueous acid and then with water.

The process according to the invention allows the preparation of, in particular, monooximes of the formula III,

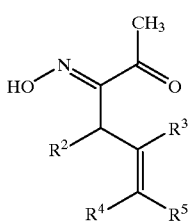

mono(oxime ethers) of the formula IV

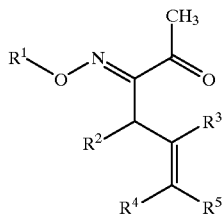

and bis(oxime) monoethers of the formula I, where:

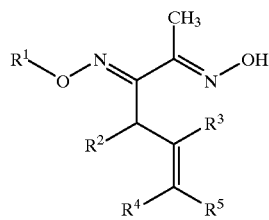

$R^1$ is unsubstituted $C_1$–$C_4$-alkyl or $C_2$–$C_4$-alkenyl-, $C_2$–$C_4$-alkynyl- or phenyl-substituted methyl;

$R^2$,$R^4$ independently of one another are hydrogen or methyl;

$R^3$,$R^5$ independently of one another are hydrogen or $C_1$–$C_4$-alkyl, trifluoromethyl or phenyl.

As illustrated by the compounds I in Scheme 4, the above formulae can also be represented in a different, conformeric notation.

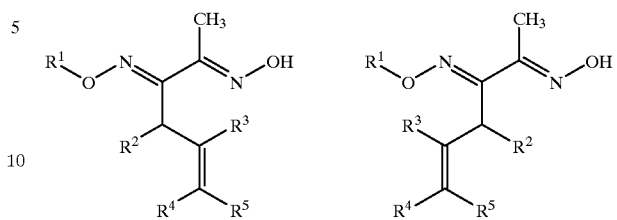

Scheme 4
possible notations for the compounds I

In the above definitions of the compounds I, II, III, IV and A, collective terms were used for the radicals $R^1$ to $R^5$ which represent individual enumerations of the individual group members. The radicals alkyl, alkenyl or alkynyl can be straight-chain or branched.

Examples of other meanings are:

halogen: fluorine, chlorine, bromine or iodine;

$C_1$–$C_4$-alkyl: methyl, ethyl, propyl, 1-methylethyl, butyl, 1-methylpropyl, 2-methylpropyl and 1,1-dimethylethyl;

$C_2$–$C_4$-alkenyl: ethenyl, prop-1-en-1-yl, prop-2-en-1-yl, 1-methylethenyl, but-1-en-1-yl, but-2-en-1-yl, but-3-en-1-yl, 1-methyl-prop-1-en-1-yl, 2-methyl-prop-1-en-1-yl, 1-methyl-prop-2-en-1-yl and 2-methyl-prop-2-en-1-yl;

$C_2$–$C_4$-alkynyl: ethinyl, 1-propinyl, 2-propinyl, 1-butinyl, 2-butinyl, 3-butinyl, 1-methyl-2-propinyl.

With respect to their suitability for use as intermediates for preparing the crop protection agents disclosed in WO-A 95/21153, WO-A 95/21154 and WO-A 97/03057, particular preference is given to the compounds of the formulae I, III and IV with the following substituents, where the preference applies in each case on its own or in combination:

$R^1$ is methyl, ethyl, benzyl or propargyl and in particular methyl or ethyl;

$R^2$,$R^4$ independently of one another are hydrogen or methyl;

$R^3$,$R^5$ independently of one another are hydrogen, methyl or trifluoromethyl.

Particular preference is given to the compounds mentioned in the 20 preparation examples below.

PREPARATION EXAMPLES

Preparation of the Monooximes III (Step a))

Example 1

5-Methylhex-5-ene-2,3-dione 3-oxime

At 10° C., 200 g of methyl 2-acetyl-4-methylpent-4-enoate (preparation: cf. Tetrahedron (1985) 4633) in 2000 ml of aqueous 10% strength potassium hydroxide solution were admixed with 85 g of sodium nitrite, and the mixture was stirred at 23° C. for 18 hours. With ice-cooling, 1000 ml of 10% strength sulfuric acid were subsequently added dropwise such that the internal temperature remained below 10° C. The mixture was then stirred at 10° C. until evolution of $CO_2$ had ceased. For work-up, the mixture was extracted with methyl tert-butyl ether, the combined organic phases were extracted with 3 N aqueous sodium hydroxide solution and the alkaline phases were adjusted to pH 1 using 20% strength sulfuric acid. They were then extracted with methylene chloride, the extract was dried over sodium sulfate and the solvent was removed under reduced pressure. This gave 142 g of the title compound as a yellow oil which crystallized on standing.

$^1$H NMR (CDCl$_3$, ppm): δ=4.8 (1H); 4.6 (1H); 3.3 (2H); 2.4 (3H); 1.8 (3H).

Preparation of the mono(oxime ethers) IV (Step b))

Example 2

5-Methylhex-5-ene-2,3-dione 3-(O-methyloxime)

141 g of 5-methylhex-5-ene-2,3-dione 3-oxime from Example 1 were dissolved in 750 ml of acetone and admixed with 165.6 g of potassium carbonate. 145 g of dimethyl sulfate in 100 ml of acetone were then added dropwise, and the mixture was stirred at 23° C. for 4 hours. The solvent was subsequently removed under reduced pressure, the residue was taken up with methyl tert-butyl ether/water and the aqueous phase was extracted repeatedly with methyl tert-butyl ether. The combined organic phases were washed with 15% strength ammonia solution and water and dried over sodium sulfate, and the solvent was removed under reduced pressure. This gave 141 g of the title compound as a yellow oil.

$^1$H NMR (CDCl$_3$, ppm): δ=4.77 (1H); 4.57 (1H); 4.0 (3H); 3.2 (2H).

Example 3

5-Methylhex-5-ene-2,3-dione 3-(O-ethyloxime)

285.7 g of 5-methylhex-5-ene-2,3-dione 3-oxime from Example 1 were dissolved in 750 ml of acetone and admixed with 335.8 g of potassium carbonate. 362 g of diethyl sulfate in 300 ml of acetone were then added dropwise, and the mixture was stirred at 23° C. for 2 hours. The solvent was subsequently removed under reduced pressure, the residue was taken up in methyl tert-butyl ether/water and the aqueous phase was extracted again with methyl tert-butyl ether. The combined organic phases were washed with 15% strength ammonia solution and water and dried over sodium sulfate, and the solvent was removed under reduced pressure. This gave 355.4 g of the title compound as a yellow oil.

$^1$H NMR (CDCl$_3$, ppm): δ=4.8 (1H); 4.6 (1H); 4.3 (2H); 3.2 (2H); 2.4 (3H); 1.7 (3H); 1.3 (3H).

Preparation of the bis(oxime) monoethers I (Step c))

Example 4

5-Methylhex-5-ene-2,3-dione 3-(O-methyloxime) 2-oxime 283.4 g of 5-methylhex-5-ene-2,3-dione 3-(O-methyloxime) in 800 ml of methanol were added dropwise to a solution of 140.6 g of hydroxylammonium chloride in 400 ml of water and 216.7 g of pyridine, and the mixture was stirred at 23° C. for 3 hours. The solvent was then removed under reduced pressure and the residue was poured into ice-water. A pH of 1 was subsequently established using 20% strength sulfuric acid and the precipitated product was filtered off with suction, taken up in methyl tert-butyl ether and washed with water. The organic phase was then dried over sodium sulfate and the solvent was removed under reduced pressure. This gave 266 g of the title compound as a colorless solid.

$^1$H NMR (CDCl$_3$, ppm): δ=9.3 (1H); 4.8 (1H); 4.6 (1H); 4.0 (3H); 3.3 (2H).

Example 5

5-Methylhex-5-ene-2,3-dione 3-(O-ethyloxime) 2-oxime 211.3 g of hydroxylammionium chloride in 400 ml of water and 240 g of pyridine were reacted with 342.4 g of 5-methylhex-5-ene-2,3-dione 3-(O-ethyloxime) in 800 ml of methanol by the method of Example 4. This gave 305 g of the title. compound as a yellowish solid.

$^1$H NMR (CDCl$_3$, ppm): δ=9.4 (1H); 4.8 (1H); 4.6 (1H); 4.2 (2H);

3.3 (2H); 2.1 (3H); 1.8 (3H); 1.3 (3H).

We claim:
1. A process for preparing bis(oxime) monoethers of the formula I,

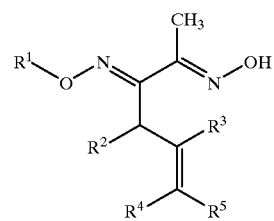

where:

R$^1$ is unsubstituted C$_1$–C$_4$-alkyl or C$_2$–C$_4$-alkenyl-, C$_2$–C$_4$-alkynyl- or phenyl-substituted methyl;

R$^2$,R$^4$ independently of one another are hydrogen or methyl;

R$^3$,R$^5$ independently of one another are hydrogen or C$_1$–C$_4$-alkyl, trifluoromethyl or phenyl, which comprises a) treating an acetoacetic ester of the formula II

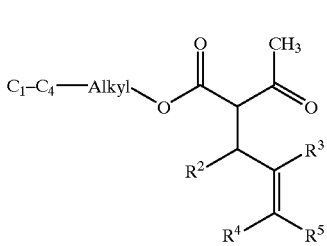

with a nitrite initially under alkaline conditions and subsequently under acid conditions and b) alkylating the resulting monooxime III

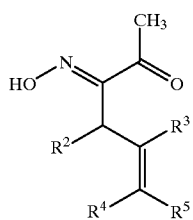
III in the presence of a base to give the mono(oxime ether) IV

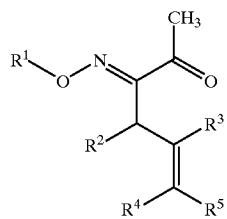
IV and finally c) reacting the mono(oxime ether) IV with hydroxylamine or its acid addition salt to give the bis(oxime) monoether I.

2. A process as claimed in claim 1, wherein in step c) the pH is set to from 5 to 7.

3. A mono(oxime ether) of the formula IV,

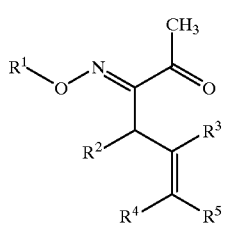
IV where:
$R^1$ is unsubstituted $C_1$–$C_4$-alkyl or $C_2$–$C_4$-alkenyl-, $C_2$–$C_4$-alkynyl- or phenyl-substituted methyl;
$R^2$,$R^4$ independently of one another are hydrogen or methyl;
$R^3$,$R^5$ independently of one another are hydrogen or $C_1$–$C_4$-alkyl, trifluoromethyl or phenyl.

4. 5-Methylhex-5-ene-2,3-dione 3-oxime.

* * * * *